(12) United States Patent
Bruza et al.

(10) Patent No.: US 7,723,285 B2
(45) Date of Patent: May 25, 2010

(54) BENEFICIAL AGENT DELIVERY SYSTEMS

(75) Inventors: Kenneth J. Bruza, Alma, MI (US);
Petar R. Dvornic, Midland, MI (US);
Addi R. Fadel, Shelton, CT (US); Jill M. Mattila, Greensboro, NC (US);
Robert M. Nowak, Midland, MI (US)

(73) Assignees: Michigan Molecular Institute, Midland, MI (US); Quest International Flavors and Fragrances Inc., Mount Olive, NJ (US)

(*) Notice: Subject to any disclaimer, the term of this patent is extended or adjusted under 35 U.S.C. 154(b) by 1196 days.

(21) Appl. No.: 11/185,128

(22) Filed: Jul. 20, 2005

(65) Prior Publication Data

US 2006/0018977 A1   Jan. 26, 2006

Related U.S. Application Data

(60) Provisional application No. 60/589,321, filed on Jul. 20, 2004.

(51) Int. Cl.
*A61K 8/00* (2006.01)
*A61K 8/18* (2006.01)
*A61Q 13/00* (2006.01)

(52) U.S. Cl. .................. 512/1; 512/2; 977/754
(58) Field of Classification Search ............... 512/1, 512/2; 977/754
See application file for complete search history.

(56) References Cited

U.S. PATENT DOCUMENTS

| | | | |
|---|---|---|---|
| 4,524,018 A | 6/1985 | Yemoto et al. | |
| 5,338,532 A | 8/1994 | Tomalia et al. | |
| 5,378,468 A | 1/1995 | Suffis et al. | |
| 5,527,524 A | 6/1996 | Tomalia et al. | |
| 5,560,929 A | 10/1996 | Hedstrand et al. | |
| 6,054,547 A * | 4/2000 | Perry et al. | 528/15 |
| 6,083,892 A | 7/2000 | Severns et al. | |
| 6,100,203 A | 8/2000 | Kil et al. | |
| 6,171,645 B1 * | 1/2001 | Smith et al. | 438/758 |
| 6,177,389 B1 | 1/2001 | Morelli et al. | |
| 6,177,414 B1 | 1/2001 | Tomalia et al. | |
| 6,239,087 B1 | 5/2001 | Mao et al. | |
| 6,350,384 B1 | 2/2002 | Dvornic et al. | |

(Continued)

FOREIGN PATENT DOCUMENTS

EP     0771785     1/2002

(Continued)

OTHER PUBLICATIONS

English machine translation of WO 9850009 A1.*

(Continued)

*Primary Examiner*—Mark Eashoo
*Assistant Examiner*—Peter F Godenschwager
(74) *Attorney, Agent, or Firm*—Price, Heneveld, Cooper, DeWitt & Litton, LLP (57) ABSTRACT

An improved fragrance delivery system capable of providing controlled release of fragrance molecules in various consumer products is composed of a polymer having covalently bound fragrance moieties that are releasable in the form of fragrance molecules. Certain embodiments comprise globular polymer particles in which unbound fragrance molecules are occluded, absorbed and/or adsorbed. Certain other embodiments incorporate fragrance monomer units, which achieve reduced residuals upon complete release of the fragrance.

2 Claims, 5 Drawing Sheets

U.S. PATENT DOCUMENTS

| | | | |
|---|---|---|---|
| 6,384,172 B1 | 5/2002 | Dvornic et al. | |
| 6,395,695 B1 | 5/2002 | Sivik | |
| 6,399,048 B1 | 6/2002 | Allard et al. | |
| 6,413,920 B1 * | 7/2002 | Bettiol et al. | 510/101 |
| 6,646,089 B2 | 11/2003 | Dvornic et al. | |
| 6,677,491 B2 | 1/2004 | Sivik | |
| 2002/0094938 A1 | 7/2002 | Dykstra et al. | |
| 2002/0155985 A1 | 10/2002 | Miracle et al. | |
| 2002/0161113 A1 * | 10/2002 | Dvornic et al. | 525/100 |
| 2003/0032565 A1 * | 2/2003 | Sivik | 510/101 |
| 2003/0073607 A1 | 4/2003 | Smets et al. | |
| 2003/0171250 A1 | 9/2003 | Smets et al. | |
| 2003/0181540 A1 | 9/2003 | Quellet et al. | |
| 2003/0211960 A1 | 11/2003 | Smets | |
| 2003/0212234 A1 | 11/2003 | Dvornic et al. | |
| 2004/0048754 A1 | 3/2004 | Herrmann et al. | |
| 2004/0110648 A1 | 6/2004 | Jordan, IV et al. | |

FOREIGN PATENT DOCUMENTS

| | | |
|---|---|---|
| EP | 0877732 | 4/2002 |
| EP | 0922084 | 11/2002 |
| WO | 94/13258 | 6/1994 |
| WO | 95/15742 | 9/1995 |
| WO | WO 9734986 A1 * | 9/1997 |
| WO | 98/28339 | 7/1998 |
| WO | 98/28398 | 7/1998 |
| WO | WO 9850009 A1 * | 11/1998 |
| WO | 00/02982 | 1/2000 |
| WO | 00/68352 | 11/2000 |
| WO | 01/79303 | 10/2001 |
| WO | WO 02077074 A1 * | 10/2002 |
| WO | 2004/067584 | 8/2004 |

OTHER PUBLICATIONS

"Dendritech, Inc., Pamam Dendrimers" from website http://www.dendritech.com/pamam.html, accessed Nov. 3, 2008.*

* cited by examiner

BENEFICIAL AGENT DELIVERY SYSTEMS

CROSS REFERENCE TO RELATED APPLICATION

This application claims priority under 35 U.S.C. §119(e) on U.S. Provisional Application No. 60/589,321 entitled HYPERBRANCHED POLYMER CONJUGATES, filed Jul. 20, 2004, by Petar R. Dvornic et al., the entire disclosure of which is incorporated herein by reference.

FIELD OF THE INVENTION

This invention relates to beneficial agent delivery systems, and more specifically to controlled release beneficial agent delivery systems that release fragrance molecules and/or other beneficial agents (e.g., artificial tanning agents) over a prolonged period of time.

BACKGROUND OF THE INVENTION

Perfumes or fragrances comprising fragrance molecules or components are utilized in various household products to improve the aesthetics associated with their use. Examples of products that contain fragrance molecules include deodorants, skin-care products, laundry detergent compositions (both liquid and granular), household cleaning compositions, fabric softeners, hair care products (including shampoos and conditioners), air fresheners, cosmetic preparations, and personal cleaning products (such as soaps and bath gels). The use of fragrances in such products is generally recognized as being essential for achieving consumer acceptance. However, fragrance molecules are generally highly volatile, especially the so-called "top notes" which are generally regarded as essential for delivering a "fresh" or "clean" odor to substrates, such as skin, hair or clothing. The highly volatile top notes of a perfume composition are typically lost during use, or even during storage, and especially upon prolonged heating, such as in a clothes dryer. Accordingly, there is a recognized need for releasing fragrance components, especially the more volatile top notes, at a controlled rate for various consumer products.

In the case of laundry detergent compositions, it is desirable to increase the amount of perfume carried over from an aqueous laundry or cleaning bath onto fabrics, and thereafter release the fragrance molecules at a controlled rate. Similarly, it is desirable to control the rate of release of fragrance molecules deposited on various substrate surfaces, such as hair and/or skin during use of personal cleansing compositions and/or hair-care products.

There have been various attempts to achieve controlled or sustained release of fragrance molecules from a variety of consumer products utilizing encapsulation techniques and/or pro-perfumes. Micro-encapsulation and inclusion complexes with specific materials such as cyclodextrins have been used to decrease volatility, improve stability and provide slow-release properties of perfuming ingredients. However, when contacted with an aqueous medium, cyclodextrin-based systems release the fragrance immediately, which limits their use as controlled release systems. Specifically, this characteristic limits the use of cyclodextrin encapsulation for most consumer products, including skin-care products, hair-care products, laundry detergent compositions, household cleaning compositions, personal cleansing products, etc., which are generally used in an aqueous environment, or at least in the presence of moisture. Other known encapsulation techniques, such as spray-drying, coacervation, and extrusion, are generally unsatisfactory for use in most consumer products, because they do not provide suitable substantivity on a substrate, i.e., an insufficient quantity of perfume ingredients are deposited and adhered on the substrate.

The use of perfume delivery systems comprising perfume molecules absorbed onto a polymeric carrier material has also been explored. While these systems provide an improvement of deposition of perfume in certain applications, these systems do not allow controlled release of the perfume over a prolonged period of time. Specially, most of the known fragrance delivery systems comprising perfume molecules absorbed on a polymeric carrier material release fragrance at a rate that is not significantly prolonged.

WO 2004/067584 discloses a perfume delivery system comprising perfume molecules absorbed onto micro-particles or nano-particles that have been modified at their surfaces to provide prolonged release of the perfume molecules, while also enhancing substantivity (i.e., adherence to a substrate). The particles are obtained by dispensing at least one hydrophobic monomer into a medium wherein the corresponding polymer is not soluble. The medium comprises an initiator, a cross-linking agent and at least one stabilizer to provide a suspension, dispersion or mini-emulsion. The medium is heated to induce polymerization and form spherical hydrophobic polymer particles. Optionally, un-reacted monomers are removed. A chemical agent capable of chemically modifying the particles to transform hydrophobic moieties into hydrophilic moieties at the surface of the particles is added. Fragrance molecules are then absorbed into the particles to provide a sustained perfume delivery system. However, the '584 publication discloses that purification in the preparation of the perfume delivery system is essential to avoid any un-reacted monomer from contaminating the perfuming ingredients.

There has also been considerable interest in research relating to the use of pro-fragrances, in which a fragrance molecule is reversibly associated (i.e., covalently bonded) with a carrier molecule to provide controlled release of the fragrance molecule from the carrier. Examples of pro-fragrances include the Michael addition reaction products of a primary and/or secondary amine compound with an unsaturated ester, acid or nitrile perfume compound. Disclosed amine compounds include polyethyleneimines, such as those commercially available under the "Lupasol" trade name. Another example of a pro-fragrance comprises the reaction product of a primary and/or secondary amine compound with a combination of a perfume ketone component and a high boiling point perfume aldehyde component. The resulting product is said to exhibit a multi-odor benefit to surfaces with which it has been contacted. Further examples of known pro-fragrances that have been said to provide laundry detergent compositions that impart a long-lasting freshness or clean scent to fabrics include ketals and acetals that release fragrance alcohols by hydrolysis of an orthoester.

Various publications have suggested the use of dendrimers as carriers for encapsulating fragrance components. Dendrimers are extremely regular in structure and mono-disperse (i.e., have essentially a single molecular weight without any significant variance).

While the use of pro-fragrances has provided some improvement in delaying the release of the more volatile and/or more soluble fragrance components, it would be desirable to achieve better control of adhesion or substantivity of fragrance molecules to specific substrates, such as textiles, skin, hair, etc., and be able to activate time release over a desired prolonged period. Further, in other cases, it would also be desirable to provide better control of the solubility of fragrance conjugates in liquid media, such as water during washing and/or rinsing cycles. There is also a broader need for developing perfume delivery systems for various consumer products to provide delayed or controlled release of fragrance molecules from substrates, such as skin, hair and textiles.

SUMMARY OF THE INVENTION

The invention provides a beneficial agent delivery system comprised of globular polymer particles having covalently bound beneficial agent moieties that are releasable in the form of beneficial agent molecules. Optionally, the particles may include absorbed or adsorbed fragrance molecules or other beneficial agents to provide release of the same or different beneficial agent molecules by different release mechanisms, such as bond cleavage and desorption.

The globular shape of the polymer particles allows attachment of beneficial agent molecules to the exterior surface of the particles and/or incorporation of beneficial agent monomeric units into the particle interior, and entrapment (e.g., absorption and/or adsorption) of the same or different beneficial agent molecules within the interior of the polymer particles. This provides different mechanisms for controlled release of beneficial agent molecules from the particles.

These and other features, advantages and objects of the present invention will be further understood and appreciated by those skilled in the art by reference to the following specification, claims and appended drawings.

DESCRIPTION OF PREFERRED EMBODIMENTS

The beneficial agent delivery systems of this invention include globular polymer particles having covalently bound beneficial agent moieties that are releasable in the form of beneficial agent molecules, and polymers comprising beneficial agent monomeric units.

The expression "polymer" is intended to encompass homopolymers, copolymers, etc. The expression "copolymer" is intended to encompass polymers comprising two or more different monomeric units. The polymers used in the practice of this invention typically have a globular or generally spherical shape, with preferred polymers including nanoparticles prepared in a mini-emulsion, micro-particles prepared in a micro-emulsion, and dendritic polymers, including hyperbranched polymers and dendrimers. The nano-particles prepared in a micro-emulsion polymerization system typically have a dimension, (e.g., diameter for a spherical particle, or largest dimension of length for an oblong particle) of from about 50 to 500 nanometers. The micro-particles prepared in a micro-emulsion polymerization system typically have a major dimension of from about 0.5 to 5 micrometers. Dendritic polymers typically have a major dimension ranging from about 1 nanometer (e.g., for a zero generation dendrimer or lower molecular weight hyperbranched polymer) to about 50 nanometers or more (e.g., for a tenth generation dendrimer or higher molecular weight hyperbranched polymer). Thus, the polymer delivery systems of this invention can have a major dimension in a range from about 1 nanometer to about 5 micrometers, or combinations having generally any particle size distribution desired within the range of from about 1 nanometer to about 5 micrometers.

The expression "monomeric unit" refers to a recurring polymer moiety that may be linked to the same or a different polymer moiety. In the case of a homopolymer, there is only one type of monomeric unit. A copolymer having at least two different monomeric units can have alternating monomeric units, randomly distributed monomeric units (e.g., random copolymer), or blocks of repeating monomeric units. In general, a polymer is synthesized from one or more monomers that correspond with the monomeric units of the polymer.

A "fragrance monomeric unit" is a monomeric unit that, when in its corresponding form as a monomer, stimulates a pleasant olfactory response. Typically, fragrance monomers include lower molecular weight (e.g., typically less than 300 Daltons) alcohols, aldehydes, ketones, esters, acetates, and nitrites that have suitable reactive functionalities for polymerization and stimulate a pleasant olfactory response.

A "beneficial agent" is a molecule that provides a beneficial effect, typically a desirable aesthetic effect when deposited on a substrate such as fabrics, skin or hair. Examples of beneficial agents include fragrance molecules, flavors, and artificial tanning agents (e.g., dihydroxyacetone) (DHA)).

A "globular polymer particle" refers to a polymer particle that is substantially spherical. Non-dendritic globular polymers (such as randomly cross-linked spherical polymer particles) can be produced by micro-emulsion polymerization or mini-emulsion polymerization. Dendritic polymers, particularly dendrimers and hyperbranched polymers, generally have a globular shape. Substantially spherical polymers are characterized by a low aspect ratio, i.e., a ratio of minimum dimension to maximum dimension of a single particle that is low, typically less than 2, and desirably less than 1.5. A perfectly spherical particle has an aspect ratio of 1.0, since its dimension in any direction is the same as in any other direction (and is equal to its diameter).

Hyperbranched polymers prepared using conventional synthesis techniques that are well-known to those having ordinary skill in the art inherently produce polymer particles having a globular shape (i.e., a substantially spherical shape). Accordingly, hyperbranched polymers are well-suited as carriers for fragrance molecules because of their molecular architecture and inherent chemical and/or physical properties. An important property of hyperbranched polymers that make them particularly well-suited for delivering fragrance molecules to substrates and releasing the fragrance molecules is the extremely high density of surface functional groups, relatively broad molecule weight distributions, and substantially spherical or globular shape.

Because of the relatively high density of reactive functional groups that reside mostly at the periphery, and are exo-presented toward the surrounding medium, hyperbranched polymers are capable of undergoing a wide variety of different chemical reactions with a number of different reagent molecules, including various fragrance molecules, which may be reversibly associated with the hyperbranched polymer and released in a controlled manner after being deposited on a substrate. Thus, hyperbranched polymers can provide a very high molecular concentration of fragrance molecules per hyperbranched polymer host molecule. Similar products cannot be achieved using traditional linear polymer carriers which typically have very few reactive groups (most frequently one at each terminal) or a multitude of side groups that are sterically hindered by the polymer chain due to coiling and which therefore are not easily accessible to attachment reactions.

Another important characteristic of hyperbranched polymers that makes them well-suited for the delivery of fragrance molecules to a substrate is their relatively broad molecular weight distribution, which can be controlled by selecting an appropriate synthesis strategy. By controlling the molecular weight and molecular weight distribution of the hyperbranched polymers, it is possible to control the time-release of fragrance molecules from the hyperbranched polymer. It is also possible to control the solubility and/or substantivity (absorptivity or adhesiveness) of the fragrance delivery systems by appropriate modification of the exo-presented terminals of the hyperbranched polymer. Specifically, as will be discussed in further detail later, a fraction or portion of the exo-presented reactive functional groups can be reacted with a substantivity-enhancing moiety and/or a solubility-enhancing moiety, while another fraction or portion of the exo-presented reactive functional groups can be reversibly reacted with a fragrance molecule. Solubility and substantivity may also be controlled by selection of an appropriate molecular weight distribution. Higher molecular weight hyperbranched polymers will release fragrance molecules more slowly because of steric hindrance effects, whereas lower molecular weight hyperbranched polymers will release fragrance molecules at a relatively higher rate. In general, dispersability and/or solubility of a hyperbranched polymer decreases as the molecular weight increases. This property, combined with the ability to modify solubility by chemically modifying the surface of the hyperbranched polymer, permits a high degree of flexibility in the design of fragrance delivery systems having a desired solubility or a desired solubility distribution. This improved flexibility and ability to distribute properties (such as solubility and substantivity) is an advantage that hyperbranched polymers have over the structurally related dendrimers, which are well-known for their pronounced mono-dispersity and lack of molecular weight distribution. The mono-dispersity and lack of molecular weight distribution of dendrimers make dendrimers considerably less well-suited for providing time-distributed properties, including time-release of fragrances.

Another important characteristic of hyperbranched polymers that makes them particularly suited for delivery of fragrances is their globular shape. The globular shape of hyperbranched polymer molecules facilitates the design of fragrance delivery systems that include fragrance moieties covalently bound to exterior functional groups of the hyperbranched polymer, which may be released, such as by hydrolysis, and the same or different fragrance molecules entrapped (i.e., occluded, adsorbed or absorbed) within the interior of the hyperbranched polymer. This provides multiple mechanisms for achieving controlled release of fragrance molecules from the system.

A further advantage of hyperbranched polymers that make them suitable for the delivery of beneficial agents to substrates is that the multiplicity of functional end-groups on the periphery of hyperbranched polymers can be used to attach various types of beneficial agent molecules, such as fragrance molecules, and/or property-controlling groups. For example, solubility-controlling moieties, such as polyethylene glycol chains may be attached to the functional groups of the hyperbranched polymer to increase water solubility. As another example, hydrocarbons, organosilicon, fluorocarbon, fluorosilicons or other organic moieties can be attached to the functional end-groups of the hyperbranched polymer to increase the solubility of the hyperbranched polymer in an organic medium. Similarly, other property-controlling moieties, such as substantivity-enhancing moieties can be attached to the functional end-groups of the hyperbranched polymer. Substantivity-enchancing moieties include long-chain hydrophobic moieties, such as hydrocarbon moieties having five or more carbon atoms, particularly linear or slightly branched olefinic or aliphatic moieties.

Thus, hyperbranched polymers are well-suited for designing controlled release polymer fragrance systems.

Similar to dendrimers, hyperbranched polymers are polymers having branches upon branches. However, in contrast to dendrimers, hyperbranched polymers are typically prepared in a one-step, one-pot procedure. This facilitates the synthesis of large quantities of materials, at high yields, and at a relatively low cost. However, the properties of hyperbranched polymer molecules are considerably different from dendrimers due to imperfect branching and rather large polydispersities, both of which are governed mainly by statistics in the synthesis of hyperbranched polymers. Hyperbranched polymers may be viewed as intermediate between randomly branched polymers and dendrimers. More specifically, a hyperbranched polymer contains a mixture of linear and fully branched repeating units, whereas an ideal dendrimer contains only fully branched repeating units, without any linear repeating units. The degree of branching, which reflects the fraction of branching sites relative to a perfectly branching system (i.e., an ideal dendrimer), for a hyperbranched polymer is greater than zero and less than 1, with typical values being from about 25% to 45%. Unlike ideal dendrimers which have a polydispersity of 1, hyperbranched polymers have a polydispersity that typically increases with increasing molecular weight, with typical polydispersities being greater than 1.1 even at relatively low molecular weight such as 1,000 Daltons, and with polydispersities greater than 1.5 being common for hyperbranched polymers having a molecular weight of about 10,000 or higher. These differences between the polydispersities and degree of branching of hyperbranched polymers as compared with dendrimers is indicative of the relatively higher non-ideality, randomness, and irregularity of hyperbranched polymers as compared with dendrimers, and distinguishes hyperbranched polymers from dendrimers.

Hyperbranched polymers that may be used to prepare the fragrance delivery systems of this invention, include various random hyperbranched polymers or controlled hyperbranched polymers that can be solubilized (either in an aqueous solvent or an organic solvent) and in which soluble guest molecules, complexes or ions can be introduced into the interior of the hyperbranched polymer molecule, and/or covalently or ionically bonded to the reactive terminal groups of the hyperbranched polymer molecule. In this regard, fragrance molecules may be associated with a hyperbranched polymer by any of a variety of chemical and/or physical mechanisms. Thus, the fragrance moiety can be associated with the hyperbranched polymer as a carried material that is physically encapsulated or entrapped (i.e., occluded) by the hyperbranched polymer, dispersed partially or fully throughout the hyperbranched polymer, or attached or linked to or into the hyperbranched polymer by means of covalent bonding, electrostatic attraction, hydrogen bonding, adsorption, absorption, metallic bonding, van der Waals forces or ionic bonding, or any combination thereof. The association of the fragrance molecule and the hyperbranched polymer may optionally employ connectors and/or spacers to facilitate the preparation or use of the hyperbranched polymer conjugates. Suitable connecting groups are groups which link a beneficial agent to the hyperbranched polymer without significantly impairing the effectiveness of the beneficial agent. These connecting groups may be cleavable or non-cleavable and may be used in order to avoid steric hindrance between the beneficial agent and the hyperbranched polymer. Preferably, the connecting groups are stable (i.e., non-cleavable). A cleavable connecting group is a connecting group in which a chemical bond present in the original connecting group, as compared to bonds found between the connecting group and the fragrance moiety connected by the connecting groups, can be broken during normal use of the beneficial agent delivery compounds.

The hyperbranched polymers of this invention may be prepared by any applicable polymerization method, including: (a) mono-molecular polymerization of $AB_2$, $AB_3$, or in general $AB_x$ or $A_xB_y$ monomers, wherein A and B are moieties that are reactive with each other but not with themselves, x and y are integers having a value of at least 2; (b) di- or multi-molecular polymerization of $A_2+B_3$, $A_2+B_4$, or in general $A_x+B_y$ monomer systems where x is an integer having a value of at least 2, and y is an integer having a value of at least 3; and (c) multi-molecular polymerization reactions of two or more polyfunctional monomers, wherein the average functionality of A or B is at least 2, while the average functionality of the other is higher than 2 (e.g., $A_2+A_x+B_2$, where x is greater than 2). Other synthesis strategies that can be employed include any of the preceding systems involving more than two types of reactive functional groups, and/or systems involving simultaneous polymerization reactions, such as multi-bond opening or ring opening reactions, step-growth polycondensations or polyadditions, and chain-growth polymerizations. In general, in order to allow synthesis and prevent premature reaction of $AB_x$ and $A_xB_y$ monomers, the A and B groups should be unreactive with each other under one set of conditions, such as at normal ambient conditions, but reactive under another set of conditions, such as in the presence of an initiator, a catalyst, heating or other type of activation.

The degree of branching of the hyperbranched polymers used in this invention is not critical. However, the degree of branching is sufficiently low (e.g., less than 95%, even less than 90%) to distinguish the hyperbranched polymers from dendrimers, which in the ideal case have a degree of branching of 100%. The hyperbranched polymers used in this invention will typically have a degree of branching less than 55%, and more typically from about 25% to about 45%. Such hyperbranched polymers can be easily prepared and are relatively inexpensive as compared with dendrimers.

The hyperbranched polymers of this invention typically have a polydispersity that is greater than 1.1, and more typically greater than 1.2. Typical polydispersities may range from about 1.2 for lower molecular weight hyperbranched polymers (e.g., those having a molecular weight of about 1,000 Daltons) to 2 or higher for higher molecular weight hyperbranched polymers (those having a molecular weight of 10,000 Daltons or more).

The hyperbranched polymers of this invention typically have a weight average molecular weight of about 25,000 Daltons or less. However, higher molecular weight hyperbranched polymers may be used, but are not typically preferred because they are more difficult and expensive to prepare, and are not believed to provide a clearly discernable advantage. The hyperbranched polymers used for this invention should generally have a molecular weight of at least about 1,000 Daltons.

In accordance with an aspect of this invention, it has been surprisingly discovered that it is possible to form conjugates between hyperbranched polymers and guest molecules, ions or elements, such as zero-valent metals, wherein the hyperbranched polymer has a weight average molecular weight less than 14,000 Daltons (approximately the molecular weight of a Generation 4 PAMAM dendrimer), with a suitable weight average molecular weight range being from about 1,000 Daltons to about 10,000 Daltons.

The hyperbranched polymer conjugates of this invention may be used for delivering various fragrance molecules to a substrate and releasing the beneficial agent in a desired controlled manner at the substrate. Examples of substrates on which the hyperbranched polymer conjugates may be deposited for subsequent release of fragrance molecules include fabrics, skin and hair. The hyperbranched polymer beneficial agent delivery systems of this invention may be utilized in various fabric care products, such as detergents, fabric softeners, etc., personal care products, including shampoos, hair conditioning products, skin care products, skin cleansing products, and the like, and products that deliver topically active agents, such as artificial tanning agents.

Hyperbranched beneficial agent delivery systems in accordance with this invention may be prepared by contacting a hyperbranched polymer with a beneficial agent molecule, complex or ion in a suitable solvent medium that will allow the beneficial agent to diffuse into and enter the interior of the hyperbranched polymer molecule and become constrained within the hyperbranched polymer molecule. Preferred fragrance molecules or other beneficial agents that are constrained within the interior of a hyperbranched polymer molecule are beneficial agents that do not readily diffuse outwardly from the interior of the hyperbranched polymer molecule when the conjugate is in a particular medium, i.e., solubilized in an aqueous solvent or in an organic solvent, as appropriate, depending on the surface functionality of a hyperbranched polymer molecule, but will be released in the absence of the particular medium, such as on a dry substrate surface or in the presence of a different medium. Constraint or occlusion of a beneficial agent within a hyperbranched polymer molecular may be achieved by contacting a beneficial agent with a hyperbranched polymer in a first solvent that causes the hyperbranched polymer to swell and occlude materials, drying the hyperbranched polymer with the occluded fragrance molecule, and dispersing the hyperbranched polymer containing the occluded fragrance molecule in a different solvent media that causes contraction of the hyperbranched polymer and retention of the fragrance molecule.

Beneficial agent delivery systems in accordance with the present invention may also be prepared by reacting a beneficial agent molecule with the reactive terminal functional groups of the hyperbranched polymer, either directly or through a linking moiety. Hyperbranched polymers having suitable reactive terminal functional groups may be prepared by appropriate selection of monomers during the synthesis of the hyperbranched polymer. For example, it is well known to prepare hyperbranched polymers having terminal reactive groups such as amino, hydroxy, mercapto, carboxy, alkenyl, nitrile, allyl, vinyl, amido, halo, urea, oxiranyl, aziridinyl, oxazolinyl, imidazolinyl, sulfonato, phosphonato, isocyanato, and isothiocyanato. Alternatively, the terminal groups of a hyperbranched polymer may be modified to provide different functional groups, such as by reacting the existing terminal groups of a hyperbranched polymer with a difunctional or polyfunctional linker having at least one functional group that is reactive with the functional groups of the hyperbranched polymer, and at least one other functional group that may be subsequently reacted with a functional group on a fragrance molecule. Partial modification of the reactive terminal functional groups of the hyperbranched polymer may be achieved by appropriate control of the stoichiometry during surface modification reactions. Difunctional and/or polyfunctional hyperbranched polymers may be used for selectively reacting with different types of fragrance molecules to provide a hyperbranched polymer fragrance delivery system that includes at least two different types of fragrance molecules. Hyperbranched polymer conjugates having two or more different fragrance molecules or moieties and optionally substantivity-enhancing moieties, may also be prepared by reacting a fragrance molecule and/or substantivity-enhancing moieties having a reactive functional group with the reactive terminals of the hyperbranched polymer in less than stoichiometric proportions so that not all of the terminal groups on the hyperbranched polymer are reacted, and subsequently reacting the remaining terminal groups with a fragrance molecule or substantivity-enhancing agent. Such techniques may also be used for modifying the solubility characteristics of the hyperbranched polymer. For example, molecules may be occluded in a hyperbranched polymer by contacting a water-soluble hyperbranched polymer with a water-soluble molecule that is to be occluded, such contact occurring for example in the aqueous phase of an emulsion, and subsequently reacting the terminal groups of the hyperbranched polymer with a lipophilic molecule, such reaction occurring for example at an aqueous-lipid interface of the emulsion, whereby the hyperbranched polymer is converted into a lipophilic particle containing occluded hydrophilic fragrance molecules.

Thus, by a suitable selection or synthesis technique, and appropriate reactions and/or occlusion techniques, it is possible to provide a hyperbranched polymer beneficial agent delivery systems having a high molecular concentration of fragrance molecules covalently bonded to the periphery and/or interior of the hyperbranched polymer molecule, and/or absorbed, solubilized, occluded, or otherwise entrapped within the interior of the hyperbranched polymer molecule. By appropriate selection or synthesis of the hyperbranched polymer it is also possible to vary the molecular weight, polydispersity and molecular weight distribution to allow differential release rates of covalently attached fragrance molecules due to varying steric effects dependent on the molecular weight and molecular weight distribution of the hyperbranched polymers.

In addition to entrapped beneficial agents and/or beneficial agents covalently bonded to the terminal reactive groups of the hyperbranched polymer, it is possible to attach other moieties to the same hyperbranched polymer molecules in order to control other properties of the hyperbranched polymer beneficial agent delivery systems, such as solubility, and substantivity or adhesion to substrates. For example, attachment of polyethylene glycol moieties will enhance hydrophilicity, while attachment of hydrocarbons, fluorocarbons, organosilicons, fluorosilicons, or other organic moieties will enhance oleophilicity.

Accordingly, utilizing the techniques and principles of the present invention, it is possible to design hyperbranched polymer conjugates that will provide an optimum combination of properties such as the ability to release a fragrance molecule and/or other beneficial agent in a controlled manner over a predetermined period of time, solubility in aqueous and/or organic solvents, and absorption to substrates, such as textiles, plastics, skin and hair.

Encompassed within the concept of a polymer fragrance delivery system is a polymer that is comprised partially or entirely of fragrance molecules as building blocks or monomeric units. In this case, the building blocks or monomer units constitute a fragrance moiety that can be released as a fragrance molecule. Each of the fragrance monomeric units in the hyperbranched polymer is reversibly bound or incorporated as part of the polymer. For these polymers, the fragrance molecules must have mutually reactive functionalities that will enable polymerization. Examples of fragrance molecules that can be reacted alone or in combination to produce polymers include vanillin, ethyl vanillin, hydroxycitronellal, and kovanol. Also encompassed within the concept of the invention are copolymers including at least one monomer that is (in its monomeric form) a fragrance molecule. Examples of copolymers of this type include copolymers of vinyl ether monomers and odorant comonomers containing a hydroxyl (OH—) group, such as dihydromyrcenol.

Figure 1:
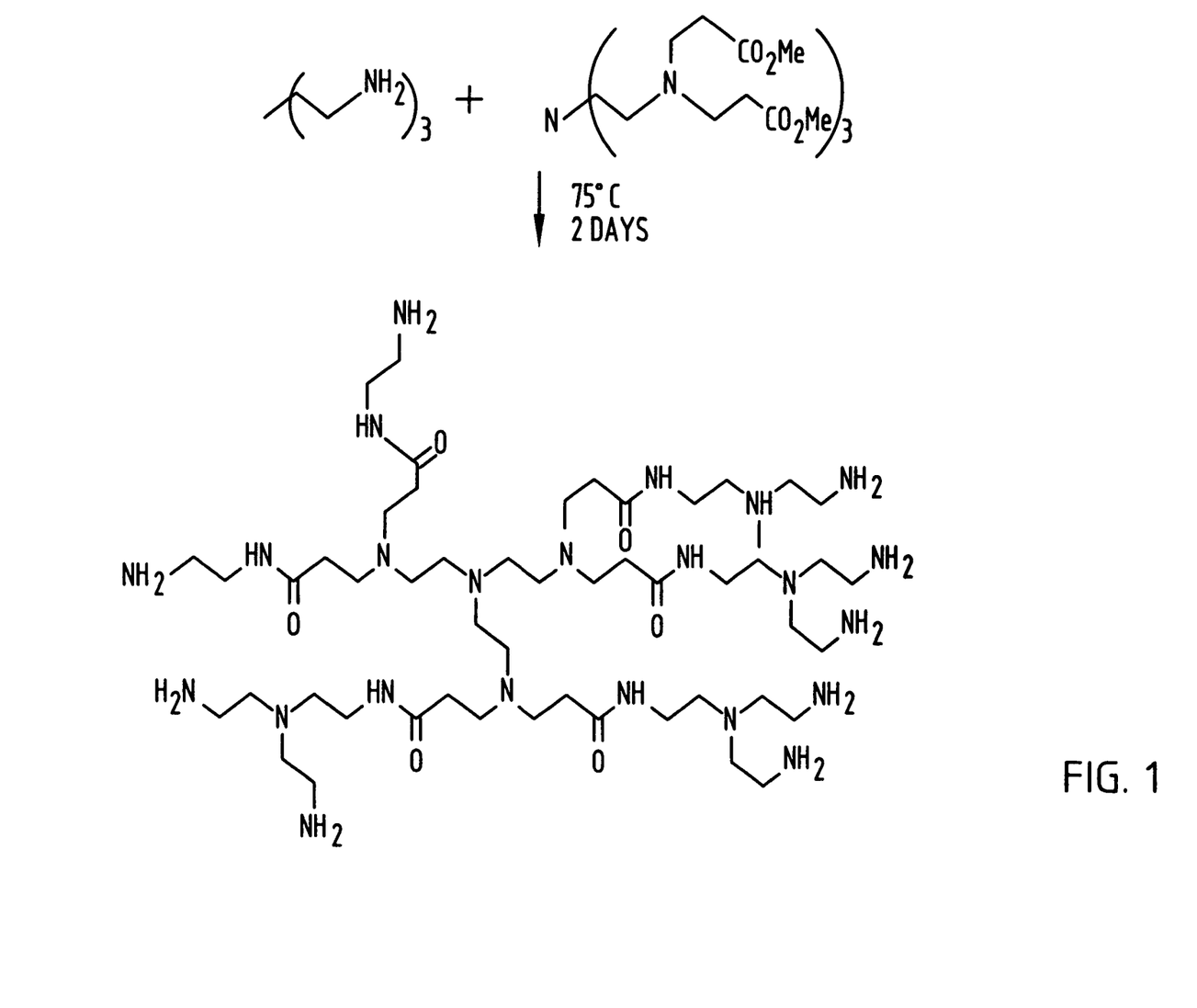
FIG. 1 is schematic illustration of synthesis of a hyperbranched polymer molecule having primary amine terminals.

Synthesis of a hyperbranched polymer molecule having primary amine terminals is illustrated in FIG. 1. As illustrated by the chemical mechanism shown in FIG. 2, the amine terminal groups bonded to a polymer backbone or polymer core (P) may be reacted with an aldehyde fragrance molecule and/or a ketone fragrance molecule to form a hyperbranched polymer fragrance delivery system having fragrance moieties that can be hydrolyzed to release aldehyde fragrance molecules and/or ketone fragrance molecules via a reverse Schiff base reaction mechanism.

Figures 2, 3:
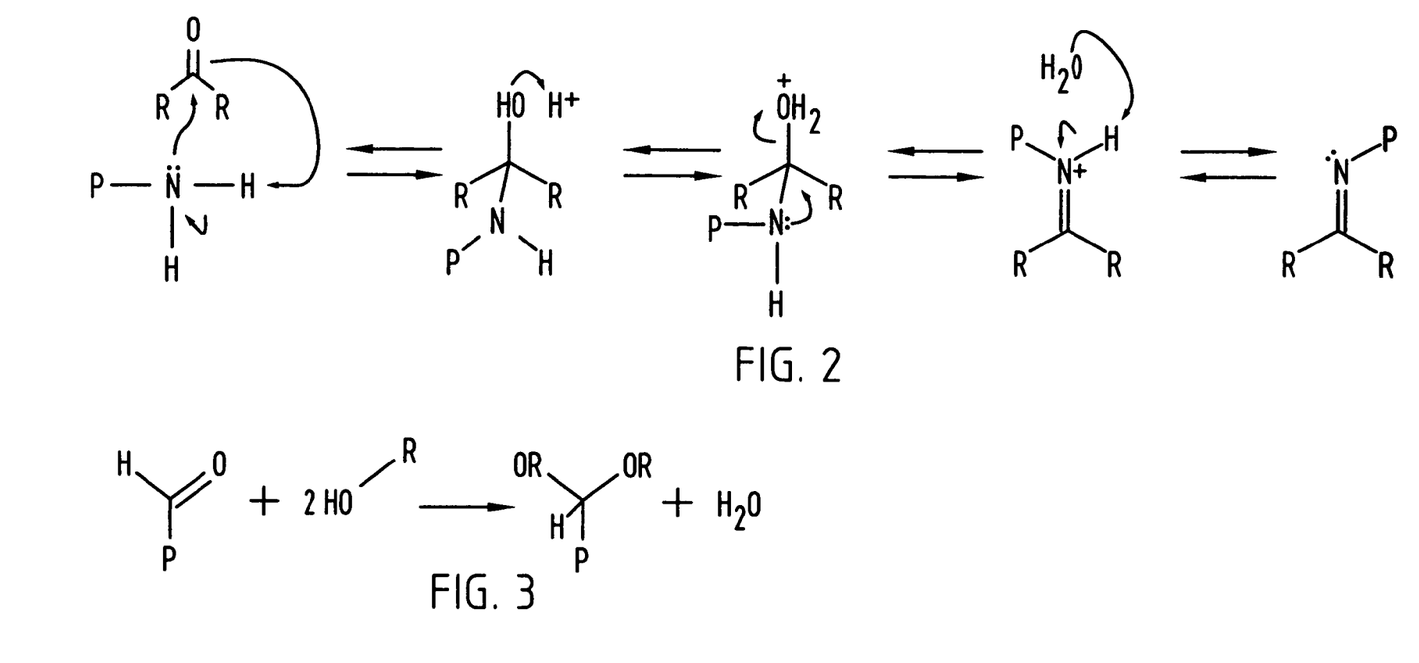
FIG. 2 is a schematic representation of the chemical mechanism by which amine terminal groups bonded to a polymer can be reacted with an aldehyde fragrance molecule to form a hyperbranched polymer fragrance delivery system.
FIG. 3 is a schematic illustration of a reaction of a polymer having a plurality of aldehyde terminal groups with fragrance alcohol molecules to provide a polymer fragrance delivery system reaction product.

FIG. 3 schematically illustrates a reaction of a polymer having a plurality of aldehyde (HCO) terminal groups (only one of which is shown) bonded to a polymer backbone or polymer core (P), each of which is reacted with two fragrance alcohol molecules to prepare a polymer fragrance delivery system having a plurality of alcohol fragrance moieties covalently bonded to the polymer, and which can be released in the form of alcohol fragrance molecules by hydrolysis upon exposure to moisture.

Figure 4:
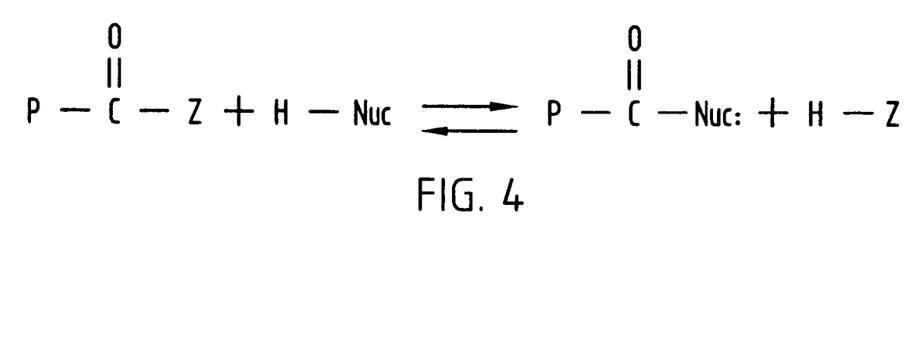
FIG. 4 is a schematic representation of the preparation of a polymer fragrance delivery system comprising nucleophilic moieties covalently bonded to a carbonyl moiety on a polymer core or backbone.

FIG. 4 schematically illustrates preparation of a polymer fragrance delivery system comprising nucleophilic moieties (Nuc) covalently bonded to a carbonyl moiety (—C=O) on a polymer core or backbone (P). The fragrance delivery system is prepared by reacting a polymer having a core or backbone (P) and a plurality of acyl groups (—COZ, only one of which is shown) with a fragrance molecule having a nucleophilic moiety (Nuc). The nucleophilic odorant molecule is releasable from the polymer via a hydrolysis reaction upon exposure to moisture. Non-limiting examples of Z-groups include halogens, such as chlorine and bromine, alcohol residues (—OR), carboxylic acid residues (—OCOR) and primary amine residues (—NHR), wherein R is typically an organic moiety, and more typically a hydrocarbon moiety, such as an aliphatic or aromatic moiety. Non-limiting examples of nucleophilic moieties include: hydroxyl groups, alcohol residues (—OR), ester residues (—OCOR), primary amine groups (—NH$_2$) and secondary amine groups (—NHR), wherein R is typically an organic group, and more typically a hydrocarbon group, such as an aliphatic or aromatic group.

Figure 5:
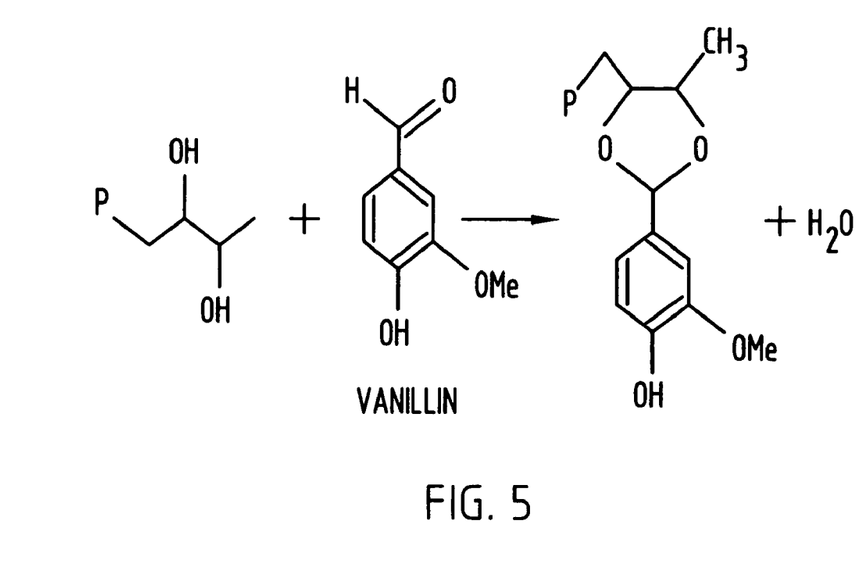
FIG. 5 is a schematic representation of a reaction of a polymer having a plurality of diol groups with vanillin to form a polymer fragrance delivery system.

FIG. 5 schematically illustrates the reaction of a polymer having a backbone or core (P) and a plurality of diol groups (—CH$_2$CHOHCHOHCH$_3$, only one of which is shown) with vanillin to form a polymer fragrance delivery system that releases the fragrance vanillin by hydrolysis upon exposure to moisture.

Figure 6:
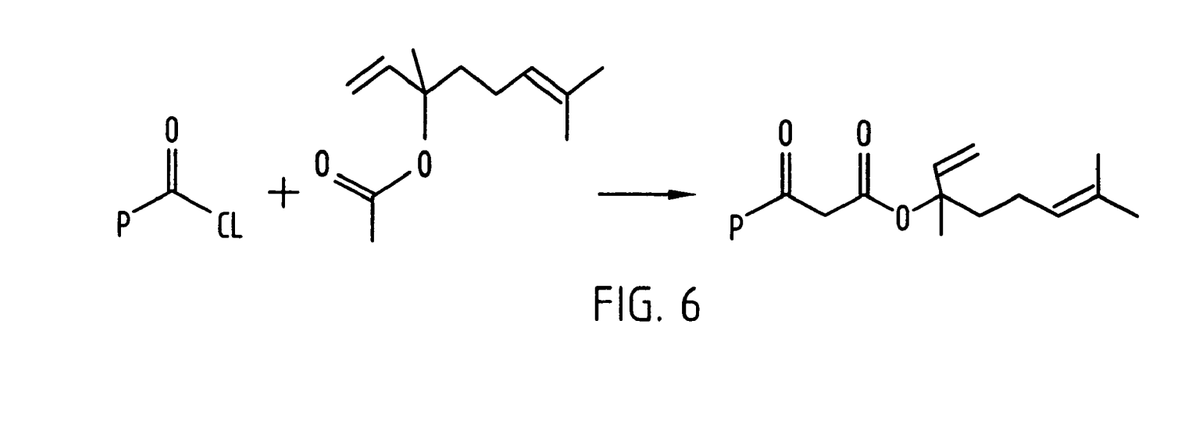
FIG. 6 is a schematic representation showing the preparation of a polymer capable of releasing linalyl acetate fragrance.
Figure 7:
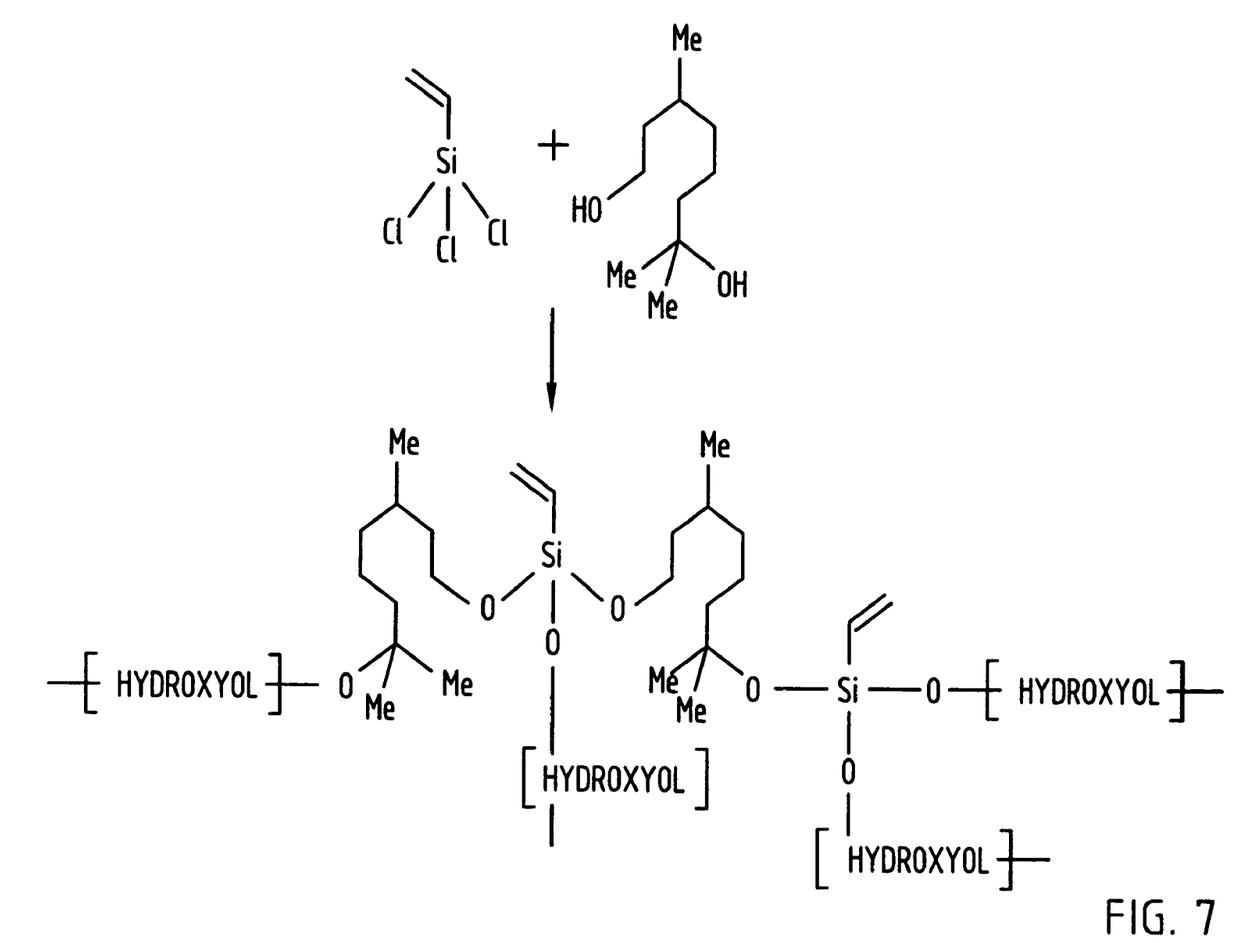
FIG. 7 is a schematic representation showing synthesis of a hyperbranched silyl hydroxyol by reacting a trichlorosilane and hydroxyol.

FIG. 6 schematically illustrates the preparation of a polymer capable of releasing linalyl acetate fragrance, which is prepared by reacting a polymer having a backbone or core P and a plurality of acyl chloride terminals (only one of which is shown) with linalyl acetate.

The polymer cores or backbones (P) referenced above may be hyperbranched polymers, other dendritic polymers, including dendrimers, or non-dendritic polymers, including linear polymers and lightly branched polymers.

The fragrance molecules used for synthesizing polymers comprising fragrance monomer units in the main polymer architecture must have at least two reactive functionalities. When the fragrance monomer includes only two reactive functionalities, it can be reacted with a comonomer having at least three reactive functionalities in order to prepare hyperbranched copolymers. Hyperbranching of such monomers can take place as long as precautions are taken to prevent cross-linking into insoluble gels. This can be accomplished as is known in the art by appropriate adjustment of the x/y molar ratio. Hence, one can synthesize a hyperbranched polymer from two different fragrance molecules as long as the two molecules have functional groups that are mutually reactive and at least one of the monomers includes at least three functional groups and the other includes at least two functional groups. If the A-B linkage formed during the preparation of the hyperbranched polymer can be reversed under the use conditions, these polymers will time-release the component monomers (e.g., such as by hydrolysis), thus providing novel delivery systems.

Suitable fragrance molecules typically have a Clog P of at least 2, a boiling point temperature less than 300° C., and a molecular weigh less than 300 Daltons. Fragrance compounds that may be associated with the hyperbranched polymers in accordance with the principles of this invention, (e.g., by occlusion, reaction with terminal functional groups on the hyperbranched polymer, or by polymerization or copolymerization of the fragrance molecules) include various well-known odoriferous compounds, such as perfumery alcohols, aldehydes, and ketones. While it is neither practical nor possible to provide an exhaustive list of known odoriferous compounds, a partial list includes the following alcohols: eugenol, 2-cyclohexyl-1-propanol, 1-decanol, geraniol, nerol, 3,7-dimethyl-1-octanol, citronellol, 1-dodecanol, ethyl vanillin, 2-ethyl-1-hexanol, 1-hexanol, pipol, vegetol, 4-hydroxy-3-methoxybenzaldehyde (vanillin), 4-(4-hydroxy-1-phenyl)-2-butanone (raspberry ketone), 7-p-menthan-1-ol (Mayol®, origin: Firmenich SA, Geneva, Switzerland), anisic alcohol, guaiacol, 2-methoxy-2-phenyl-1-ethanol, isoeugenol, cyclomethylene citronellol, 2-methyl-4-phenyl-1-pentanol, 2-methyl-5-phenyl-1-pentanol, 3-methyl-5-phenyl-1-pentanol, 6-nonen-1-ol, 2,6-nonadien-1-ol, 1-octanol, 2-phenoxy-1-ethanol, 1-phenyl-1-ethanol, 2-phenyl-1-ethanol, 2-phenyl-1-propanol, 3-phenyl-1-propanol, cinnamic alcohol, salicylates, 2,4,6-trimethyl-3-cyclohexene-1-methanol, farnesol, 3,5,5-trimethyl-1-hexanol, 1-undecanol, 10-undecen-1-ol, patchone, 2-tert-butyl-4-methyl-1-cyclohexanol (rootanol), 6,8-dimethyl-2-nonanol, 4,8-dimethyl-7-nonen-2-ol, (E)-3,3-dimethyl-5-(2',2',3'-trimethyl-3'-cycl-openten-1'-yl)-4-penten-2-ol (Polysantol®; origin: Firmenich SA, Geneva, Switzerland), ethyl 3-hydroxy hexanoate, 5-ethyl-2-nonanol, dartanol, 3-hydroxy-2-butanone, 1-(4-isopropyl-1-cyclohexyl)-1-ethanol, menthol, 8-p-menthen-2-ol, isopulegol, 7-methoxy-3,7-dimethyl-2-octanol, 2-methoxy-4-propyl-1-cyclohexanol (Tarragol®; origin: Firmenich SA, Geneva, Switzerland), 4-methyl-3-decen-5-ol (origin: Givaudan SA, Geneva, Switzerland), 1-(4-methylphenyl)-1-ethanol (methyl paratolyl carbinol), 4-methyl-1-phenyl-2-pentanol, 1,2,3,4,4a,5,8,8a-octahydro-2,2,6,8-tetramethyl-1-naphthalenol, 3-methyl-5-(2,2,3-trimethyl-3-cyclopenten-1-yl)-2-pentanol (origin: Givaudan SA, Geneva, Switzerland), 2-octanol, 3-octanol, 1-octen-3-ol, 3,4,5,6,6-pentamethyl-2-heptanol (kohinol), 2-pentyl-1-cyclopentanol (cyclopentol), 4-phenyl-2-butanol, 4-phenyl-3-buten-2-ol, 1-phenyl-2-hexanol, 1-phenyl-2-pentanol, 1-phenyl-2-propanol, limbanol, fenchol, borneol, 3-(5,5,6-trimethyl-bicyclo[2.2.1]hept-2-yl)-1-cyclohexanol (Sandela®; Givaudan), vebanol, 4-(2,6,6-trimethyl-1-cyclohexen-1-yl)-3-butenol (beta-ionol), alpha-ionol, norlimbanol, 2-undecanol, 3-benzyl-3-pentanol, 4-cyclohexyl-2-methyl-2-butanol (origin: Firmenich SA, Geneva, Switzerland), 2,6-dimethyl-2-heptanol, ethyl linalool, 3,7-dimethyl-1,6-octadien-3-ol (linalool), 3,7-dimethyl-3-octanol (tetrahydrolinalool), 2,6-dimethyl-2-octanol (tetrahydromyrcenol), 2,6-dimethyl-7-octen-2-ol (dihydromyrcenol), hydroxycitronellal, 8-p-menthanol, terpinenol, alpha-terpineol, methyl-4-phenyl-2-butanol, 2-methyl-1-phenyl-2-propanol, 2-(4-methylphenyl)-2-propanol, perhydro-4,8a-dimethyl-4a-naphthalenol (geosmin), tetrahydro-2-isobutyl-4-methyl-4(2H)-pyranol (Florol®; origin: Firmenich SA, Geneva, Switzerland), linalyl oxide, 2,6,10,10-tetramethyl-1-oxaspiro[4.5]decan-6-ol (spiranol), 2,6,6,8-tetramethyl-tricyclo[5.3.1.0(1,5)]undecan-8-ol (cedrenol), nerolidol and pinanol; the following aldehydes: citral, citronellal, campholenic aldehyde, cinnamic aldehyde, hexylcinnamic aldehyde, formyl pinane, hydroxycitronellal, cuminic aldehyde, vanilline, ethyl vanilline, Lilial® [3-(4-tert-butylphenyl)-2-methylpropanal; origin: Givaudan-Roure SA, Vernier, Switzerland], Lyral® [4- and 3-(4-hydroxy-4-methylpentyl)-3-cyclohexene-1-carbaldehyde; origin: International Flavors and Fragrances, USA], Bourgeonal® [3-(4-tert-butylphenyl)propanal; origin: Quest International, Naarden, Netherlands], heliopropanal [3-(1,3-benzodioxol-5-yl)-2-methylpropanal; origin: Firmenich SA, Geneva, Switzerland], Zestover (2,4-dimethyl-3-cyclohexene-1-carbaldehyde; origin: Firmenich SA, Geneva, Switzerland), Trifernal® (3-phenylbutanal; origin: Firmenich SA, Geneva, Switzerland), α-sinensal, (4-methylphenoxy)acetaldehyde, 1,3-benzodioxol-5-carboxaldehyde (heliotropine), Scentenal® [8(9)-methoxy-tricyclo[5.2.1.0.(2,6)]decane-3(4)-carbaldehyde; origin: Firmenich SA, Geneva, Switzerland], Liminal® [(4R)-1-p-menthene-9-carbaldehyde; origin: Firmenich SA, Geneva, Switzerland], Cyclosal [3-(4-isopropylphenyl)-2-methylpropanal; origin: Firmenich SA, Geneva, Switzerland], ortho- and para-anisaldehyde, 3-methyl-5-phenylpentanal, Acropal® [4-(4-methyl-3-pentenyl)-3-cyclohexene-1-carbaldehyde; origin: Givaudan-Roure SA., Vernier, Switzerland], Intreleven® aldehyde (mixture of 10-undecenal and 9-undecenal; origin: International Flavors & Fragrances, USA), muguet aldehyde [(3,7-dimethyl-6-octenyl)acetaldehyde; origin: International Flavors & Fragrances, USA], 2,6-dimethyl-5-heptanal, Precyclemone® B [1-methyl-4-(4-methyl-3-pentenyl)-3-cyclohexen-1-carbaldehyde; origin: International Flavors & Fragrances, USA] and Isocyclocitral® (2,4,6-trimethyl-3-cyclohexene-1-carbaldehyde; origin: International Flavors & Fragrances, USA); and the following ketones: camphor, carvone, menthone, ionones, irones, damascenones and damacones, benzyl acetone (4-phenyl-2-butanone), 1-carvone, 4-(4-hydroxy-1-phenyl)-2-butanone (raspberry ketone), Hedione® (methyl dihydrojasmonate; origin: Firmenich SA, Geneva, Switzerland), Neobutenone [1-(5,5-dimethyl-1-cyclohexen-1-yl)-4-penten-1-one; origin: Firmenich SA, Geneva, Switzerland], Calone200 (7-methyl-2H,4H-1,5-benzodioxepin-3-one; origin: C.A.L. SA, Grasse, France), Sulfox [(1R,4R)-8-mercapto-3-p-menthanone; origin: Firmenich SA, Geneva, Switzerland], Orivone® [4-(1,1-dimethylpropyl)-1-cyclohexanone; origin: International Flavors & Fragrances, USA], Delphone (2-pentyl-1-cyclopentanone; origin: Firmenich SA, Geneva, Switzerland), 2-naphthalenyl-1-ethanone, Veloutone (2,2,5-trimethyl-5-pentyl-1-cyclopentanone; origin: Firmenich SA, Geneva, Switzerland), 4-isopropyl-2-cyclohexen-1-one, Iso E Super® [isomer mixture of 1-(octahydro-2,3,8,8-tetrame-2-naphthalenyl)-1-ethanone; origin: International Flavors & Fragrances, USA], Plicatone [5-methyl-exo-tricyclo[6.2.1.0(2,7)]undecan-4-one; origin: Firmenich SA, Geneva, Switzerland]; and macrocyclic ketones such as, for example Exaltone® (cyclopentadecanone), Delta-Muscenone (mixture of 3-methyl-4-cyclopentadecen-1-one and 3-methyl-5-cyclopentadecen-1-one) and muscone (3-methyl-1-cyclopentadecanone), all from Firmenich SA, Geneva, Switzerland.

Flavor molecules that may be utilized in the practice of this invention are generally similar to and substantially overlap with the suitable fragrance molecules, the difference being primarily their intended use in edible food products. Flavor molecules bonded to hyperbranched polymers and/or hyperbranched polymers polymerized or copolymerized from flavor molecules may release the individual flavor molecules such as by hydrolysis upon mastication of a food product containing the beneficial agent delivery compounds in accordance with this invention.

The beneficial agent delivery compounds of this invention may also be utilized for delivering various topically active agents to human and/or animal skin. Examples of topically active agents that may be conjugated with hyperbranched polymers and used in accordance with the principles of this invention include artificial tanning agents, analgesics, anti-inflammatory agents, antimicrobials, penetration enhancing agents, etc. Examples of artificial tanning agents include dihydroxyacetone, isatin, alloxane, ninhydrin, glyceraldehyde, mesotartaric aldehyde and pyrazoline-4,5-dione derivatives. Examples of analgesics include benzocaine, dyclonine hydrochloride, and aloe vera. Examples of anti-inflammatory compounds include alclometasone, dipropionate, betamethasone, valerate, etc. Examples of antimicrobials include antifungals such as miconazole nitrate, benzalkonium chloride, benzethonium chloride, benzoic acid, benzoyl peroxide, benzyl alcohol, etc. Examples of penetration enhancing agents include dimethylsulfoxide, dimethyl formamide, N,N-dimethylacetamide, decylmethylsulfoxide, polyethylene glycol monolaurate, 1-substituted azacycloheptan-2-ones, etc.

The beneficial agent delivery compounds of this invention may be utilized in various personal care products, such as shampoos, deodorants, soaps, lotions and the like. Accordingly, an aspect of the invention relates to the provision of personal care products, in liquid or solid form, comprising one or more surfactants, a beneficial agent delivery compound comprising a hyperbranched polymer and a beneficial agent associated with the hyperbranched polymer, and, optionally other ingredients commonly contained in such products, such as conditioners, flavoring agents, coloring agents, emollients, thickening agents, etc. In accordance with another aspect of the invention the beneficial agent delivery compounds of this invention may be utilized in various liquid or granular cleaning and/or detergent compositions, such as for laundering clothes. Such compositions comprise one or more surfactants, a beneficial agent delivery compound comprising a hyperbranched polymer and a beneficial agent associated with the hyperbranched polymer (e.g., fragrance compounds), which may be incorporated in a carrier (e.g., water), and may optionally include other additives conventionally employed in detergent and/or cleansing compositions, such as detergent builders, soil release and anti-redeposition agents, processing aids, dyes or pigments, solid fillers, enzymes, bleaches, bleach activators, bleach catalysts, fabric conditioners, brighteners, preservatives, antioxidants, chelants, stabilizers, anti-shrinkage agents, anti-wrinkle agents, germicides, fungicides, anti-corrosion agents, suds boosters, etc.

The artificial tanning compositions and other compositions comprising topically active agents typically include the beneficial agent delivery compound having a hyperbranched polymer and a beneficial agent associated with the hyperbranched polymer solvated, suspended or otherwise dispersed in a carrier (e.g., a water, alcohol or hydrocarbon-based solvent system), and may include other ingredients conventionally employed in topically applied compositions, such as emollients, pigments, moisturizers, vitamins, fragrances, preserving agents, fillers, sequestering agents, etc.

Food products in accordance with an aspect of the invention comprise a nutritional edible substance and a beneficial agent delivery compound comprising a hyperbranched polymer and a beneficial agent associated with the hyperbranched polymer, wherein the beneficial agent comprises one or more flavor compounds. The beneficial agent delivery agent may be used to provide prolonged flavor delivery in foods or chewing gum, and may be used to provide changing flavors (e.g., a chewing gum that initially has a first flavor and over time during chewing of the gum develops a second flavor that is entirely different from the first flavor).

Non-dendritic globular polymer particles having a diameter or major dimension in the range from about 50 nanometers up to about 5 microns can be prepared in accordance with the techniques disclosed in WO 2004/067584 A1. More specifically, solid micro-particles and/or nano-particles formed of a single spherical cross-linked polymer can be prepared by dispensing, under stirring, a hydrophobic monomer in a medium wherein the corresponding polymer is not soluble, and wherein the medium includes an initiator, a cross-linking agent, and at least one stabilizer to provide a suspension, dispersion or mini-emulsion and heating the suspension, dispersion or mini-emulsion to induce polymerization. Examples of suitable monomers include various vinyl esters such as tert-butylacrylate, tert-butylmethacrylate, isobutyl methacrylate, n-butyl(methy)acrylate, isobutylacrylate, n-propylacrylate, isopropylmethyacrylate and norbornyl (meth)acrylate. Other suitable monomers or comonomers include vinyl aromatic amines. Desirably, at least some of the monomers have reactive functional groups such as nucleophilic groups, acyl groups, amine groups, etc., which can be reacted with a fragrance molecule to form nanoscopic and/or microscopic fragrance delivery particles. A combination of different sized particles, such as 1-50 nanometer hyperbranched polymer fragrance delivery particles, and 50 nm-5 μm substantially spherical fragrance delivery particles may be utilized in combination to provide a very broad range of possible fragrance release profiles. As with the hyperbranched polymer fragrance delivery systems, the larger (about 50 nanometers to about 5 micrometers) particles prepared by mini- or micro-emulsion polymerization may be modified at the surface to improve solubility in a particular medium and/or to enhance substantivity. Also, as with the hyperbranched polymer particles, fragrance molecules that are either the same or different from those that are released by cleavage of a covalent bond (e.g., hydrolysis), can be occluded, absorbed or adsorbed into the polymer particles to provide multiple release mechanisms.

In those cases where the polymer carrier (i.e., the backbone or core of the fragrance delivery system) is not itself comprised of fragrance monomer units, the residual materials left after release of the fragrance molecules is relatively inert and harmless. However, an advantage of utilizing polymers comprised entirely, or at least partially, of fragrance monomer units is that there is not any, or very little, residual material left after complete release of the fragrance molecules.

The fragrance delivery systems of this invention may be added to various consumer products including deodorants, skin-care products, laundry detergent compositions (both liquid and granular), household cleaning compositions, fabric softeners, hair care products (e.g., shampoos and conditioners), air fresheners, cosmetic preparations, and personal cleansing products (e.g., bath soaps and bath gels).

Hydrolysis of Hyperbranched Fragrant Polymers

Figure 8:
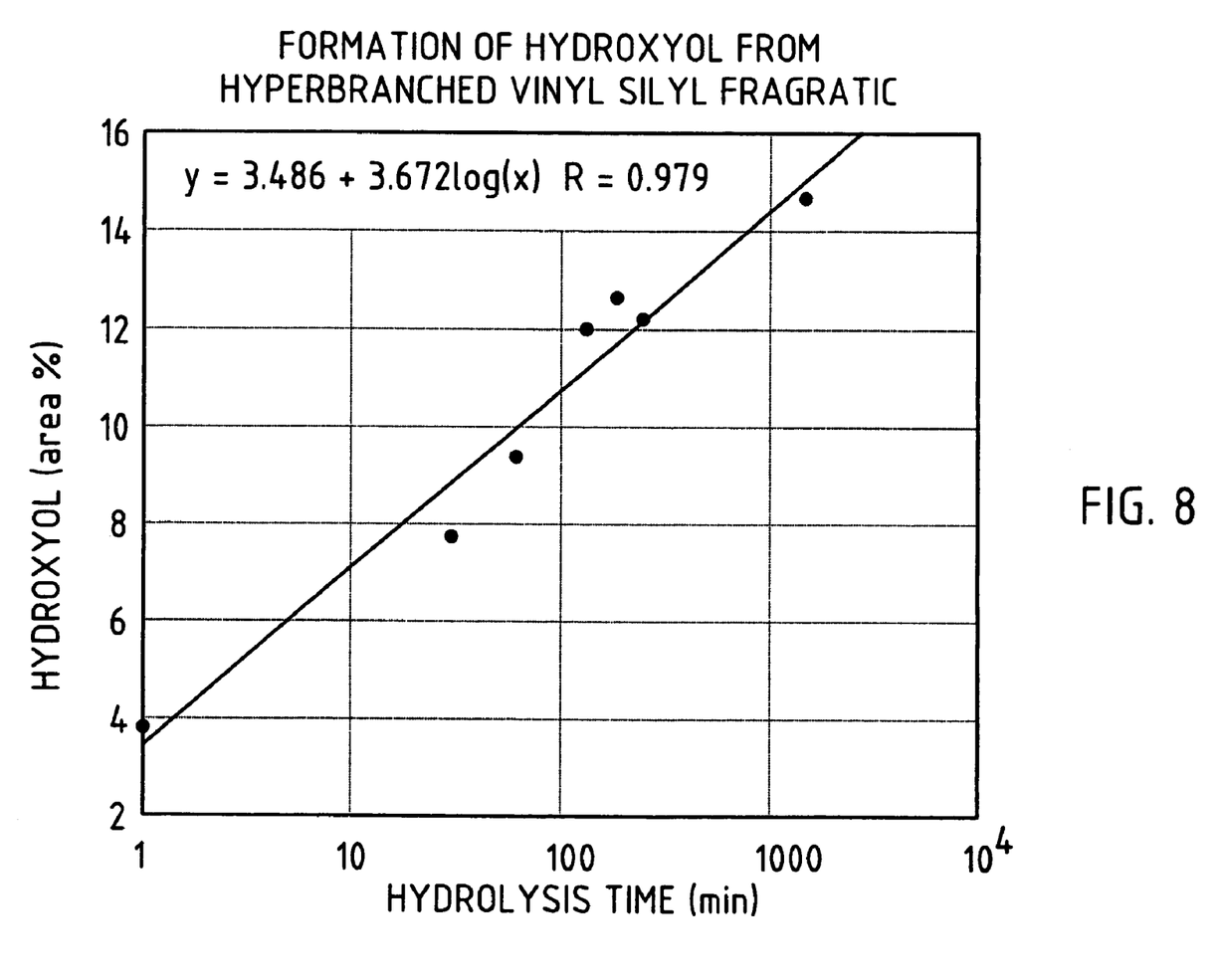
FIG. 8 is a graph showing the rate at which hydroxyol is released upon hydrolysis of a hyperbranched silyl hydroxyol polymer.

In order to determine how rapidly the hyperbranched molecules containing chemically bound fragrant diols in the branches would undergo mild acid catalyzed hydrolysis, a hyperbranched material prepared from vinyl trichlorosilane and hydroxyol was prepared as illustrated schematically in FIG. 8 was subjected to hydrolysis conditions at pH 6.86.

Synthesis of Hyperbranched Silyl Hydroxyol

Into a two-neck, 25 mL round bottom flask equipped with a magnetic stir bar, reflux condenser with nitrogen inlet and an equilibrating addition funnel with stopper was placed 3.73 g (21.4 mmol) of hydroxyol. To the gently stirring hydroxyol was added 2.304 g (14.27 mmol) of vinyl trichlorosilane, dropwise, via the addition funnel. Some frothing was observed. The addition funnel was quickly replaced with a glass tube that extended to below the level of the reaction mixture and through this glass tube was passed a steady stream of nitrogen. At the same time the nitrogen inlet on the reflux condenser was replaced with a gas take off valve which allowed the nitrogen bubbling through the reaction to escape. The temperature of the reaction mixture was then slowly raised to 65° C. over a period of several hours after which the reaction mixture was held at this temperature for 48 hours while continuing to bubble nitrogen through the liquid. At the end of this time the heating was ceased and the tube through which the nitrogen was passed into the reaction mixture was raised above the surface of the liquid. As the temperature fell to room temperature the liquid became more viscous.

FTIR shows a significantly reduced intensity —OH stretch at 3438 cm-1; strong stretches at 1121 and 1076 cm-1 (Si—O—R) and a small olefin stretch at 1601 cm-1.

GPC: Mn 1281; Mw 2572; Mz 2015 Dispersity 1.23.

Hydrolysis of Hyperbranched Silyl Hydroxyol

In a simple experiment, the hyperbranched material was mixed with an aqueous buffer solution, pH 6.86 and vigorously stirred at room temperature and under a nitrogen atmosphere. The ratio of fragrant molecule to buffer was 100 mg of hyperbranched molecule to 1.0 mL of pH 6.86 buffer solution. The hyperbranched material was not soluble in water and therefore the reaction mixture was an emulsion subject to some sampling errors due to compositional differences.

0.5 mL Aliquots of the reaction mixture were taken, diluted with tetrahydrofuran to a volume of 1.0 mL and analyzed by gas chromatography (GC), measuring the amount of hydroxyol released from the hyperbanched molecule.

| Time of Hydrolysis (Minutes) | Formation of Hydroxyl (Area %) |
|---|---|
| 1.0 | 3.80 |
| 30 | 7.77 |
| 60 | 9.44 |
| 120 | 12.03 |
| 180 | 12.70 |
| 240 | 12.38 |
| 1440 | 14.70 |

FIG. 8 shows the rate of formation of the hydroxyol under the conditions of the reaction.

Based upon the data obtained it appeared that the hydroxyol is being released at a rate of 3.2 area % per 60 minutes. Overall, if the hydrolysis is continued until total consumption of hyperbranched hydroxyol is completed, this would take approximately 2.17 days.

It is not necessarily certain that the release of hydroxyol would continue at the same observed rate as the hydrolysis proceeds. The interfacial nature between water and the hyperbranched hydroxyol may become more rate determining in the release of the hydroxyol. Also, higher molecular weight hyperbranched polysilyl alcohols in general may lead to steric blocking of both the water and the proton source, towards penetrating through the arms and branches of the hyperbranched species. This would lead to a mechanism where the surface available silicon-oxygen bonded materials would have to be hydrolyzed first before water can penetrate further into the core of the hyperbranched molecules.

Any alcohol, diol, triol or polyol which is capable of forming siloxane hyperbranched molecules, is expected to demonstrate similar behavior to the hyperbranched-hydroxyol. All of these hyperbranched materials are expected to undergo slow hydrolysis, releasing the alcohol over a prolonged period of time.

The effect of pH, or acidity is also important in the hydrolysis of siloxane hyperbranched molecules. In a model study, hydroxyol was converted to its bis-trimethylsilyl ether and subjected to acid catalyzed hydrolysis using 0.01 N HCl, pH 2.02. The reaction was followed by FT-IR and gas chromatography and it was shown that the siloxanes were hydrolyzed in several hours to yield pure hydroxyol.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the doctrine of equivalents.

The invention claimed is:

1. A hyperbranched silyl hydroxyol polymer.
2. A hyperbranched silyl hydroxyol of claim 1 that is a reaction product of a trichlorosilane and hydroxyol.

* * * * *

UNITED STATES PATENT AND TRADEMARK OFFICE
CERTIFICATE OF CORRECTION

PATENT NO. : 7,723,285 B2
APPLICATION NO. : 11/185128
DATED : May 25, 2010
INVENTOR(S) : Bruza et al.

It is certified that error appears in the above-identified patent and that said Letters Patent is hereby corrected as shown below:

Col. 4, line 40
 "nitrites" should be --nitriles--;

Col. 4, line 46
 "(DHA))." should be --(DHA).--;

Col. 9, line 54
 "systems" should be --system--;

Col. 11, line 45,
 "weigh" should be --weight--; and

Col. 16, claim 2, line 65,
 "trichiorosilane" should be --trichlorosilane--.

Signed and Sealed this

Ninth Day of November, 2010

David J. Kappos
*Director of the United States Patent and Trademark Office*